United States Patent
Han et al.

(10) Patent No.: US 11,344,584 B2
(45) Date of Patent: May 31, 2022

(54) GEMELLA SANGUINIS AS A BIOTHERAPEUTIC

(71) Applicant: Second Genome, Inc., South San Francisco, CA (US)

(72) Inventors: Andrew Wonhee Han, South San Francisco, CA (US); Bernat Baeza Raja, South San Francisco, CA (US); Shoko Kawana, South San Francisco, CA (US); Mitsuko Lynn Yamamoto, South San Francisco, CA (US); Karim Dabbagh, South San Francisco, CA (US); Todd Zachary DeSantis, South San Francisco, CA (US)

(73) Assignee: Second Genome, Inc., Brisbane, CA (US)

( * ) Notice: Subject to any disclaimer, the term of this patent is extended or adjusted under 35 U.S.C. 154(b) by 0 days.

(21) Appl. No.: 16/651,041

(22) PCT Filed: Aug. 6, 2018

(86) PCT No.: PCT/US2018/045329
§ 371 (c)(1),
(2) Date: Mar. 26, 2020

(87) PCT Pub. No.: WO2019/067087
PCT Pub. Date: Apr. 4, 2019

(65) Prior Publication Data
US 2020/0237830 A1    Jul. 30, 2020

Related U.S. Application Data

(60) Provisional application No. 62/563,124, filed on Sep. 26, 2017.

(51) Int. Cl.
| | |
|---|---|
| A61K 35/74 | (2015.01) |
| A23L 33/135 | (2016.01) |
| A61P 3/10 | (2006.01) |
| A61K 9/00 | (2006.01) |

(52) U.S. Cl.
CPC ............ *A61K 35/74* (2013.01); *A23L 33/135* (2016.08); *A61P 3/10* (2018.01); *A61K 9/0053* (2013.01)

(58) Field of Classification Search
None
See application file for complete search history.

(56) References Cited

U.S. PATENT DOCUMENTS

| | | |
|---|---|---|
| 2002/0037577 A1 | 3/2002 | Park |
| 2013/0316029 A1 | 11/2013 | Pan |
| 2014/0199281 A1 | 7/2014 | Henn |
| 2016/0158294 A1* | 6/2016 | Von Maltzahn ..... A61K 9/0053 424/93.41 |
| 2016/0331792 A1 | 11/2016 | Dominguez-Bello |

FOREIGN PATENT DOCUMENTS

WO    WO 2016/185469    11/2016

OTHER PUBLICATIONS

Altschul et al., "Basic local alignment search tool", Journal of molecular biology, Oct. 5, 1990, 215(3):403-410.
Collins et al., "Description of Gemella sanguinis sp. nov., isolated from human clinical specimens," Journal of clinical microbiology, Oct. 1, 1998, 36(10):3090-3093.
Collins et al., "Genetic vulnerability to diet-induced obesity in the C57BL/6J mouse: physiological and molecular characteristics," Physiology & behavior, Apr. 1, 2004, 81(2):7 Pages.
DeFronzo et al., "Glucose clamp technique: a method for quantifying insulin secretion and resistance," American Journal of Physiology—Endocrinology And Metabolism, Sep. 1, 1979, 237(3):E214-E223.
Dewi et al., "In vitro assessment of human endothelial cell permeability: effects of inflammatory cytokines and dengue virus infection," Journal of virological methods, Nov. 1, 2004, 121(2):171-180.
Dewi et al., "Peripheral blood mononuclear cells increase the permeability of dengue virus-infected endothelial cells in association with downregulation of vascular endothelial cadherin," Journal of General Virology, Mar. 1, 2008, 89(3):642-652.
Eid et al., "Significance of Microbiota in Obesity and Metabolic Diseases and the Modulatory Potential by Medicinal Plant and Food Ingredients," Frontiers in Pharmacology, Jun. 30, 2017, 8:387, 29 Pages.
EP Extended European Searh Report in European Appln. No. 18861799.7 dated Jun. 10, 2021, 12 pages.
Forslund et al., "Disentangling type 2 diabetes and metformin treatment signatures in the human gut microbiota," Nature, Dec. 2015, 528(7581):24 Pages.
GenBank Accession No. JWDE01000000, "Gemella sanguinis strain 1094_BTHU, whole genome shotgun sequencing project," Jul. 13, 2016, 2 pages.
GenBank Accession No. Y13364.1, "Gemella sanguinis 16S rRNA gene (strain 2045-94)," Apr. 2, 2001 [online], Retrieved on Sep. 21, 2018, Retrieved from the Internet <URL: https://www,ncbi.nlm.nih.gov/nuccore/Y13364 >, 1 page.
GenBank Locus ACRY02000000, "Gemella sanguinis M325, whole genome shotgun sequencing project," Feb. 7, 2014, 2 pages.
GenBank Locus JNJO00000000, "Gemella sanguinis ATCC 700632, whole genome shotgun sequencing project," Jun. 11, 2014, 2 pages.
Henao-Mejia et al., "Role of the intestinal microbiome in liver disease," Journal of autoimmunity, Oct. 1, 2013, 46:66-73.
Hung Wei-Chun et al., "*Gemella parahaemolysans* sp. Nov. and *Gemella taiwanensis* sp. Nov., isolated from human clinical specimens," Int. J. of Systematic and Evolutionary Microbiology., Jun. 2015, 64:6:2060-2065.

(Continued)

*Primary Examiner* — Brian Gangle
(74) *Attorney, Agent, or Firm* — Fish & Richardson P.C.

(57) ABSTRACT

The disclosure relates to live biotherapeutic products, probiotics, pharmaceutical compositions comprising said probiotics, and methods of using them to treat various human diseases. In some aspects, the disclosure provides such compositions comprising strains of the bacterium *Gemella sanguinis* and their uses in treating metabolic-related diseases or disorder.

19 Claims, 5 Drawing Sheets

Specification includes a Sequence Listing.

(56) References Cited

OTHER PUBLICATIONS

Johnson et al., "Microbiome and metabolic disease: revisiting the bacterial phylum Bacteroidetes," Journal of Molecular Medicine, Jan. 1, 2017, 95(1):1-8.
Karlsson et al., "Gut metagenome in European women with normal, impaired and diabetic glucose control," Nature, Jun. 2013, 498(7452):99-103.
Leitner et al., "Mapping of human brown adipose tissue in lean and obese young men," Proceeding of the National Academy of Sci., Jul. 2017, 114:32:8649-8654.
Lindstrom, "The Physiology of Obese-Hyperglycemic Mice [ob/ob Mice]," Scientific World Journal Jan. 1, 2007, 7:666-685.
Maffeis et al., "Association between intestinal permeability and faecal microbiota composition in Italian children with beta cell autoimmunity at risk for type 1 diabetes: Gut permeability and microbiota in T1D," Diabetes Metabolism Res. And Rev., March 206, 32:7:700-709.
Mandic et al., "Evaluation of head and neck squamous cell carcinoma invasiveness by the electrical resistance breakdown assay," Clinical & experimental metastasis, Jun. 1, 2005, 21(8):699-704.
Nathan et al., "The Effect of Intensive Treatment of Diabetes on the Development and Progression of Long-Term Complications in Insulin-Dependent Diabetes Mellitus", The Diabetes Control and Complications Trial Research Group, New England journal of medicine, Sep. 30, 1993, 329(14):977-986.
Palau-Rodriguez et al., "Metabolomic insights into the intricate gut microbial-host interaction in the development of obesity and type 2 diabetes," Frontiers in Microbiology, Oct. 27, 2015, 6:1151, 12 pages.
PCT International Preliminary Report on Patentability in International Appln. No. PCT/US2018/045329, dated Mar. 31, 2020, 8 pages.
PCT International Search Report and Written Opinion in International Application No. PCT/US2018/45329, dated Oct. 23, 2018, 13 pages.
Pippitt et al., "Diabetes Mellitus: Screening and Diagnosis," American Family Physician, Jan. 15, 2016, 93(2):103-109.
Pool-Zobel et al., "Overview of experimental data on reduction of colorectal cancer risk by inulin-type fructans," The Journal of nutrition, Nov. 1, 2007, 137(11):2580S-2584S.
Qin et al., "A metagenome-wide association study of gut microbiota in type 2 diabetes," Nature, Oct. 2012, 490(7418):55-60.
Ramirez-Farias et al., "Effect of inulin on the human gut microbiota: stimulation of Bifidobacterium adolescentis and Faecalibacterium prausnitzii," British Journal of Nutrition, Jul. 2008, 101(4):541-550.
Said et al., "Dybosis of salivary microbiota in inflammatory bowel disease and its association with oral immunological biomarkers," DNA Res., Sep. 2013, 21:1:15-25.
Sweeney et al., "The human gut microbiome: a review of the effect of obesity and surgically induced weight loss," JAMA Surgery, Jun. 1, 2013, 148(6):11 Pages.
Tang et al., "Gut Microbiota in Cardiovascular Health and Disease," Circulation research, Mar. 31, 2017, 120(7):1183-1196.
Tatusova et al., "BLAST 2 Sequences, a new tool for comparing protein and nucleotide sequences," FEMS microbiology letters, May 1, 1999, 174(2):247-250.
Tatusova et al., "Erratum to BLAST 2 Sequences, a new tool for comparing protein and nucleotide sequences," [FEMS Microbiol. 1999, 174:247-250], FEMS Microbiology Letters, Aug. 1, 1999, 177(1):1 Page.
Tremaroli et al., "Roux-en-Y Gastric Bypass and Vertical Banded Gastroplasty Induce Long-Term Changes on the Human Gut Microbiome Contributing to Fat Mass Regulation," Cell metabolism, Aug. 4, 2015, 22(2):12 Pages.
Vandamme et al., "Polyphasic taxonomy, a consensus approach to bacterial systematics," Microbiological reviews, Jun. 1, 1996, 60(2):407-438.
Yang et al., "The gut microbiota: a key regulator of metabolic diseases," BMB reports, Oct. 31, 2016, 49(10):536-541.
Yarza et al., "Uniting the classification of cultured and uncultured bacteria and archaea using 16S rRNA gene sequences," Nature Reviews Microbiology, Sep. 2014, 12(9):635-645.
Yassour et al., "Sub-clinical detection of gut microbial biomarkers of obesity and type 2 diabetes," Genome medicine, Dec. 2016, 8:17, 14 pages.
Zeevi et al., "Personalized Nutrition by Prediction of Glycemic Responses," Cell, Nov. 19, 2015, 163(5):17 Pages.
Zheng et al., "Gut microbiome in type 1 diabetes: A comprehensive review," Diabetes Metabolism Res. And Rev., Jul. 2018, 34:7:33043.

\* cited by examiner

Epididymal fat

Subcutaneous fat

GEMELLA SANGUINIS AS A BIOTHERAPEUTIC

CROSS-REFERENCE TO RELATED APPLICATIONS

This application is a National Stage Application under 35 U.S.C. § 371 of International Application No. PCT/US2018/045329, filed on Aug. 6, 2018, which claims the benefit of priority to U.S. Provisional Application No. 62/563,124, filed on Sep. 26, 2017, each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: SEGE_020_01WO_SeqList_ST25.txt, date created, Aug. 2, 2018, file size ≈2.3 kilobytes.

FIELD

The present disclosure relates to novel and therapeutically effective compositions and methods for therapeutic treatment comprising live bacteria. The microbial compositions have application, inter alia, in regaining healthy glucose homeostasis in a subject. Envisioned are uses of the compositions in the treatment, amelioration and/or prevention of hyperglycemia, diabetes, and conditions and disease states associated with abnormal metabolic regulation and/or gastrointestinal disorders.

BACKGROUND

The microbiome of the gastrointestinal tract comprises a diverse array of microorganisms, primarily prokaryotes, which play a significant role in the health of the host organism. The complexity of the microbiome, in terms of both its population makeup and composite function, has recently become an intense area of study as research increasingly shows that manipulation of the microbiome can provide health benefits and may be effective in treating a number of diseases and disorders. Currently, a number of probiotics are marketed which contain live bacteria and yeast and are believed to augment the benefits of these microbes which naturally occur in the human body. Increasingly, live biotherapeutic products (LBPs) are being developed for controlled clinical studies and regulatory approval in the treatment of disease. These diseases are multifaceted and present diagnostically in a myriad of ways.

There is a great need in the art for the development of a therapeutic, which can not only restore glycemic homeostasis but also treat associated complications thereof in an individual. Research has demonstrated that an improperly functioning glycemic control and regulation can lead to a diverse array of metabolic syndromes, conditions, and/or disorders. The live biotherapeutic products, probiotics, and compositions thereof as taught herein restore a number of human health aspects to a level where homeostasis can be restored and established to prevent or treat a disease, condition, or any slight imbalance in metabolic or inflammatory factors.

SUMMARY OF THE DISCLOSURE

In some embodiments, a method for treating a subject in need thereof is provided, comprising administering to the subject a composition comprising a therapeutically effective amount of live bacteria, wherein the live bacteria is *Gemella sanguinis* (*G. sanguinis*), wherein the *G. sanguinis* bacterium comprises a 16S rRNA gene that is at least 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% identical to SEQ ID NO:1.

In some embodiments, a method to treat a subject experiencing or diagnosed with hyperglycemia is provided.

In some embodiments, a method to improve glucose homeostasis in a subject is provided.

In some embodiments, the subject has been diagnosed with or is suffering from a metabolic disorder.

In some embodiments, the metabolic disorder is selected from the group consisting of hyperglycemia, hyperinsulinemia, pre-diabetes, type 1 diabetes mellitus, obesity, type 2 diabetes mellitus, metabolic syndrome, cardiometabolic risk, hypertension, dyslipidemia, insulin resistance, hyperinsulinemia, hepatic steatosis, renal disease, cardiovascular disease, cerebrovascular disease, and peripheral vascular disease. In other embodiments, the metabolic disorder is selected from the group consisting of hyperglycemia, insulin resistance, and type 2 diabetes. In still other embodiments, the metabolic disorder is hyperglycemia.

In some embodiments, the subject has not been diagnosed with type 2 diabetes. In other embodiments, the subject has not been diagnosed with type 1 diabetes.

In some embodiments, the subject has presented with a fasting blood glucose level of greater than about 125 mg/dL or 130 mg/dL.

In some embodiments, the subject has presented with a 2-hour value for a 75-gram oral glucose tolerance test of greater than about 140 mg/dL.

In some embodiments, the administering results in a reduction of the subject's fasting blood glucose level of at least about 1%, 2%, 3%, 4%, 5%, 10%, 20%, 30% or 40% of the fasting blood glucose level of the subject prior to the first administration of the composition.

In some embodiments, the reduction of the subject's fasting blood glucose level is measured at 1 month, 2 months, 3 months, 4 months, 5 months, 6 months, 7 months, 8 months, 9 months, 10 months, 11 months, or 12 months after the first administration of the composition.

In some embodiments, the subject has been diagnosed with a gastrointestinal disorder. In other embodiments, the gastrointestinal disorder is associated with reduced intestinal epithelial barrier function. In still other embodiments, the gastrointestinal disorder is selected from the group consisting of ulcerative colitis (UC), Crohn's disease (CD), irritable bowel syndrome (IBS), GI mucositis, chemotherapy-induced mucositis, radiation-induced mucositis, necrotizing enterocolitis, pouchitis, functional diarrhea, functional dyspepsia, functional constipation, functional abdominal pain, functional bloating, Epigastric Pain Syndrome, Postprandial Distress Syndrome, gastrointestinal reflux disease (GERD), and any combinations thereof.

In some embodiments, the method comprises administering the composition to the subject once, twice or three times per day over a time period of about 1-52 weeks. In other embodiments, the method comprises administering the composition to the subject once, twice or three times per day over a time period of greater than 1 year.

In some embodiments, the *G. sanguinis* comprises a genome which is at least 90%, 91%, 92%, 93%, 94%, 95%, 96%, 97%, 98%, 99%, 99.5%, or 99.9%, 99.99%, 99.999%, or 100% identical *G. sanguinis* GenBank Locus Number JNJO00000000. In other embodiments, the percent identity is calculated over at 80%, 85%, 90%, 95%, 98%, 99%, 99.5% 99.9%, 99.99%, 99.999%, or 100% of the whole reference genome sequence. In still other embodiments, the sequence identity is calculated using the BLAST program.

In some embodiments, the *G. sanguinis* is the strain deposited as ATCC 700632.

In some embodiments, the *G. sanguinis* in the composition are viable.

In some embodiments, the therapeutically effective amount of *G. sanguinis* comprises about $1\times10^7$ to $1\times10^{12}$ colony forming units (CFU).

In some embodiments, the composition comprising the *G. sanguinis* is selected from the group consisting of a tablet, a capsule, a liquid, and a liquid suspension.

In some embodiments, the composition comprising the *G. sanguinis* is a food-based product selected from the group consisting of a yogurt, cheese, milk, meat, cream, or chocolate.

In some embodiments, the composition comprising the *G. sanguinis* is a pet food. In other embodiments, the pet is a dog, a cat, or a cow.

BRIEF DESCRIPTION OF THE FIGURES

FIG. 5A), carnitine palmitoyltransferase 1A (cpt-1α; FIG. 5B) and sterol regulatory element binding transcription factor 1 (srebf1; FIG. 5C) in a high-fat diet-induced obese mouse, as described in Example 3.

DETAILED DESCRIPTION

Definitions

Figure 1:
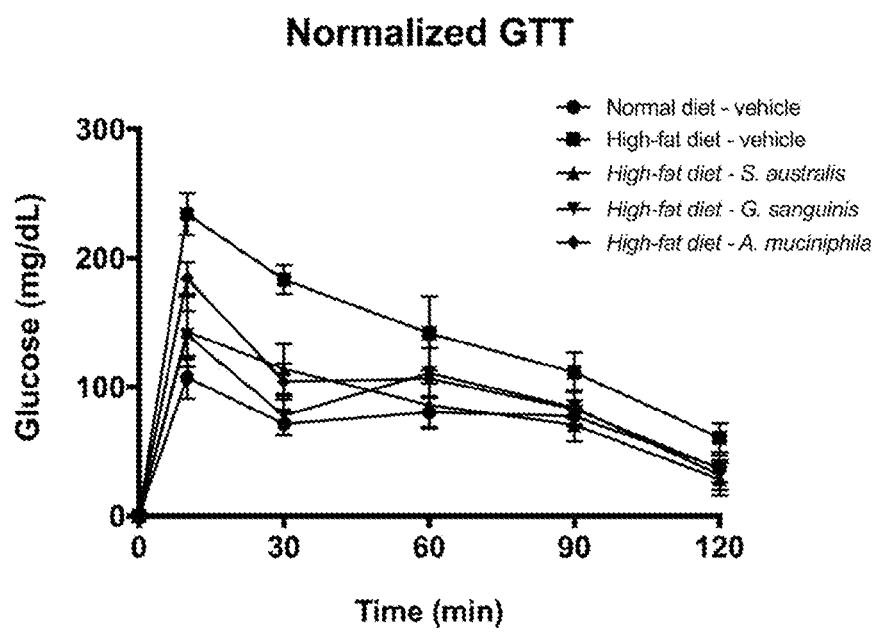
FIG. 1 shows effects of treatment with *G. sanguinis* on glucose homeostasis by presenting normalized glucose tolerance test (GTT) results in a high-fat diet-induced obese mouse, as described in Example 1.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art. Thus, while the following terms are believed to be well understood by one of ordinary skill in the art, the following definitions are set forth to facilitate explanation of the presently disclosed subject matter.

Throughout this specification, the word "comprise" or variations such as "comprises" or "comprising" will be understood to imply the inclusion of a stated component, or group of components, but not the exclusion of any other components, or group of components.

The term "a" or "an" refers to one or more of that entity, i.e. can refer to a plural referents. As such, the terms "a" or "an," "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "microorganism" or "microbe" should be taken broadly. These terms are used interchangeably and include, but are not limited to, the two prokaryotic domains, Bacteria and Archaea, as well as eukaryotic fungi and protists. In some embodiments, the disclosure refers to the "microbe." This characterization can refer to not only the identified taxonomic bacterial genera of the microbe, but also the identified taxonomic species, as well as the various novel and newly identified bacterial strains.

As used herein, "isolate," "isolated," "isolated microbe," and like terms, are intended to mean that the one or more microorganisms has been separated from at least one of the materials with which it is associated in a particular environment (for example gastrointestinal fluid, gastrointestinal tissue, human digestive fluid, human digestive tissue, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain may exist as, for example, a biologically pure culture, or as spores (or other forms of the strain) in association with a pharmaceutically acceptable carrier suitable for human administration.

In certain aspects of the disclosure, the isolated microbes exist as isolated and biologically pure cultures. As used herein the term "biologically pure" refers to a laboratory culture that is substantially free from other species of organism. Preferably, the bacterial species is in the form of a culture of a single species of organism. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. In re *Bergstrom*, 427 F.2d 1394, (CCPA 1970) (discussing purified prostaglandins), see also, In re *Bergy*, 596 F.2d 952 (CCPA 1979)(discussing purified microbes), see also, *Parke-Davis & Co.* v. *H.K Mulford & Co.*, 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co.* v. *Olin Mathieson Chemical Corp.*, 253 F.2d 156 (4th Cir. 1958) (discussing purity limitations for vitamin B12 produced by microbes), incorporated herein by reference.

In certain aspects of the disclosure, the isolated microbes also encompass the use of mutants or variants of the bacterial species or strains described herein. As used herein, the terms "mutant" and "variant" includes derived bacterial strains having at least 80% identify, at least 85% identify, at least 90% identify, at least 95% identity, at least 98%, or at least 99% identity to the genomic sequence of a referenced strain. Mutants and variants are obtainable by natural processes, mutagenesis campaigns, random culturing, and genetic engineering techniques, among others. The term "mutant" is interchangeable herein with the term "variant."

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

As used herein, "probiotic" refers to a substantially pure microbe (i.e., a single isolate) or a mixture of desired microbes, and may also include any additional components that can be administered to a subject (e.g. a human) for restoring or altering microbiota. Probiotics or microbial inoculant compositions of the disclosure may be administered with an agent to allow the microbes to survive the environment of the gastrointestinal tract, i.e., to resist low pH and to grow in the gastrointestinal environment. In some embodiments, the present compositions (e.g., microbial compositions) are probiotics in some aspects.

As used herein, "prebiotic" refers to an agent that increases the number and/or activity of one or more desired microbes. Non-limiting examples of prebiotics that may be useful in the methods of the present disclosure include fructooligosaccharides (e.g., oligofructose, inulin, inulin-type fructans), galactooligosaccharides, amino acids, alcohols, and mixtures thereof. See Ramirez-Farias et al. (2008. *Br. J. Nutr.* 4:1-10) and Pool-Zobel and Sauer (2007. *J Nutr.* 137:2580-2584 and supplemental).

As used herein, "live biotherapeutic product" or "LBP" refers to a biological product that: 1) contains live organisms, such as bacteria, and 2) is applicable to the prevention, treatment, or cure of a disease or condition of a subject in need thereof. In some embodiments, a LBP is a therapeutic composition which will undergo or has undergone clinical regulatory approval.

A "combination" of two or more bacteria includes the physical co-existence of the bacteria, either in the same material or product or in physically connected products, as well as the temporal co-administration or co-localization of the different bacteria.

The recitations "sequence identity," "percent identity," "percent homology," or for example, comprising a "sequence 50% identical to," as used herein, refer to the extent that sequences are identical on a nucleotide-by-nucleotide basis over a window of comparison. Thus, a "percentage of sequence identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity.

As used herein, sequence "identity" can be determined using standard techniques known to those skilled in the art. For example, identity may be determined using the on-line algorithm "BLAST" program, publicly available at blast.ncbi.nlm.nih.gov/Blast.cgi. Alternatively or additionally, to determine the % identity of two nucleic acid sequences, the sequences can be aligned for optimal comparison purposes (e.g., gaps can be introduced in one or both of a first and a second sequence for optimal alignment and portions of non-identical sequences can be disregarded as appropriate for comparison purposes). In certain embodiments, the length of a reference sequence aligned for comparison purposes is at least 50%, 60%, 70%, 80%, 90%, 95%, 96%, 97%, 98%, 99% or 100% of the length of the reference sequence. The nucleotides at corresponding nucleotide positions are then compared. The percent identity between the two sequences is a function of the number of identical positions shared by the sequences, taking into account the number of gaps, and the length of each gap, which need to be introduced for optimal alignment of the two sequences.

The phrases "substantially similar" and "substantially identical" in the context of at least two nucleic acids typically means that a polynucleotide comprises a sequence that has at least about 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity, in comparison with a reference polynucleotide.

The "colonization" of a host organism includes the non-transitory residence of a bacterium or other microscopic organism.

The terms "patient," "subject," and "individual" may be used interchangeably and refer to either a human or a non-human animal. These terms include mammals such as humans, non-human primates, livestock animals (e.g., bovines, porcines, ovine, caprine, poultry), companion animals (e.g., canines, felines, equine, oryctolagus) and rodents (e.g., mice and rats). In certain embodiments, the terms refer to a human patient. In exemplary embodiments, the terms refer to a human patient that suffers from, e.g., type 2 diabetes, hyperglycemia, hyperinsulinemia, obesity, a gastrointestinal inflammatory condition (e.g. IBD), or any combination thereof.

As used herein, "inhibiting and suppressing" and like terms should not be construed to require complete inhibition or suppression, although this may be desired in some embodiments. Thus, an "inhibited immune response" or the "inhibition of inflammatory cytokines" does not require absolute inhibition.

As used herein, the term "hyperglycemia" refers to the condition wherein excess glucose is in the blood stream. For example, fasting blood sugar levels greater than about 125 mg/dL or 130 mg/dL (greater than about 7 mmol/L) can be used to diagnose hyperglycemia in a subject.

As used herein, the term "obesity" refers to the condition characterized by excess body fat. For example, BMI (body mass index, $kg/m^2$) of 30 or above is considered to be obese.

The term "gut" as used herein is meant to refer to the entire gastrointestinal or digestive tract (also referred to as the alimentary canal) and it refers to the system of organs within multi-cellular animals which takes in food, digests it to extract energy and nutrients, and expels the remaining waste. As used herein the term "gastrointestinal tract" refers to the entire digestive canal, from the oral cavity to the rectum. The term "gastrointestinal tract" includes, but is not limited to, mouth and proceeds to the esophagus, stomach, small intestine, large intestine, rectum and, finally, the anus.

As used herein, the term "therapeutically effective amount" refers to an amount of a therapeutic agent (e.g., a microbe, live biotherapeutic product (LBP), and/or probiotic of the disclosure), which confers a therapeutic effect on the treated subject, at a reasonable benefit/risk ratio applicable to any medical treatment. Such a therapeutic effect may be objective (i.e., measurable by some test or marker) or subjective (i.e., subject gives an indication of, or feels an effect). In some embodiments, "therapeutically effective amount" refers to an amount of a therapeutic agent or composition effective to treat, ameliorate, or prevent (e.g., delay onset of) a relevant disease or condition, and/or to exhibit a detectable therapeutic or preventative effect, such as by ameliorating symptoms associated with the disease, preventing or delaying onset of the disease, and/or also lessening severity or frequency of symptoms of the disease.

As used herein, the term "treatment" (also "treat" or "treating") refers to any administration of a therapeutic agent (e.g., a microbe, live biotherapeutic product, and/or probiotic of the disclosure), according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., chronic or recurring immune response and inflammation of the gastrointestinal (GI) tract, chronic or recurring hyperglycemia); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, the term "medicament" encompasses medicaments for both human and animal usage in human and veterinary medicine. In addition, the term "medicament" as used herein means any substance, which provides a therapeutic and/or beneficial effect. The term "medicament" as used herein is not necessarily limited to substances, which need Marketing Approval, but may include substances which, can be used in cosmetics, nutraceuticals, food (including feeds and beverages for example), probiotic cultures, nutritional supplements and natural remedies. In addition, the term "medicament" as used herein encompasses a product designed for incorporation in animal feed, for example livestock feed and/or pet food.

"Pharmaceutical" implies that a composition, microbe, reagent, method, and the like, are capable of a pharmaceutical effect, and also that the composition is capable of being administered to a subject safely. "Pharmaceutically acceptable" means approved by a regulatory agency of the Federal or a state government or listed in the U.S. Pharmacopoeia or other generally recognized pharmacopoeia for safe use in animals, and more particularly safe use in humans. "Pharmaceutically acceptable vehicle" or "pharmaceutically acceptable excipient" refers to a diluent, adjuvant, excipient or carrier with which a microbe as described herein is administered. The preparation of a pharmaceutical composition or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by the FDA Office of Biological Standards.

The therapeutic pharmaceutical compositions taught herein may comprise one or more natural products, however, in certain embodiments, the therapeutic pharmaceutical compositions themselves do not occur in nature. Further, in certain embodiments, the therapeutic pharmaceutical compositions possess markedly different characteristics, as compared to any individual naturally occurring counterpart, or composition component, which may exist in nature. That is, in certain embodiments, the pharmaceutical compositions taught herein—which comprise a therapeutically effective amount of an isolated microbe—possess at least one structural and/or functional property that impart markedly different characteristics to the composition as a whole, as compared to any single individual component of the composition as it may exist naturally. The courts have determined that compositions comprising natural products, which possess markedly different characteristics as compared to any individual component as it may exist naturally, are statutory subject matter. Thus, the taught therapeutic pharmaceutical compositions as a whole possess markedly different characteristics. These characteristics are illustrated in the data and examples taught herein.

Details of the disclosure are set forth herein. Although methods and materials similar or equivalent to those described herein can be used in the practice or testing of the present disclosure, illustrative methods and materials are now described. Other features, objects, and advantages of the disclosure will be apparent from the description and from the claims.

Gastrointestinal Bacteria Beneficial to Metabolic Health

The composition of the intestinal microbiome has been demonstrated to be closely associated with a variety of diseases and disorders including metabolic disease and disorders (Eid et al., 2017, Front Pharmacol, 8:387), cardiovascular disease (Tang et al., 2017, Circ Res, 120:1183-1196), and liver disease (Henao-Mejia et al., 2013, J Autoimmun, 46:66-73) and has been linked to changes in glycemic control (Palau-Rodriguez, 2015, Front Microbiol, 6:1151), in both humans and animals, including animal models.

Glucose homeostasis is the maintenance of glucose tolerance within somewhat narrow physiological limits. An inability to maintain glucose tolerance can contribute to a number of detrimental downstream effects including but not limited to insulin resistance. Insulin resistance is the decreased ability of muscle, fat or liver cells to appropriately use the insulin that has been secreted by pancreatic cells into the bloodstream. As a result, more insulin may be produced to process the same amount of glucose, resulting in hyperinsulinemia. Poor glucose homeostasis in combination with insulin resistance can result in both hyperglycemia and hyperinsulinemia, leading to risk of type 2 diabetes mellitus (T2DM). Short term complications of very high blood sugar levels include ketoacidosis (harmful buildup of ketones in the blood) and hyperosmolar nonketotic syndrome. Long term complications of T2DM include diabetic retinopathy, kidney disease, diabetic neuropathy, and macrovascular problems.

Numerous studies have been carried out to analyze the gut microbiome of persons suffering from a metabolic disorder, including comparisons of the gut microbiome of these persons with that of healthy counterparts. In order to perform such studies, fecal matter from subjects of interest is collected and analyzed to determine the type, and sometimes relative quantity, of bacterial in the feces. The resultant data are indicative of each subject's gut microbiome. Specific and individual bacteria present in a sample are determined by a number of methods involving a combination of molecular and computational elements. Specifically, bacteria may be identified by identification of unique microbial 16S ribosomal RNA (rRNA) sequences (by nucleotide microarray or by sequencing) or through metagenomics analysis which can employ whole genome shotgun sequencing and assembly. The results of each method are dependent upon a number of variables ranging from sample preparation and PCR amplification to software programs used to analyze the laboratory data and parameters selected for each program.

To identify bacterial strains possessing functional importance in the metabolic health of subjects, studies which included the collection and characterization of the gut microbiome from subjects having metabolic disorders were analyzed. Such studies include comparisons of gut microbiota in subjects diagnosed with type 2 diabetes vs. healthy patients (Qin et al., 2015, 2012, Nature 490:55-60; Forslund et al., 2015, *Nature*, 528:262-266), gut microbiota from subjects before and after they had undergone Roux-en-Y gastric bypass surgery (Sweeney and Morton, 2013, JAMA Surg, 148:563-569; Tremaroli et al., 2015, Cell Metab, 22:228-238), and gut microbiota from subjects determined to be healthy or with sub-clinical disease correlated with various metabolic disease markers such as BMI, HbA1c, cholesterol levels, or glucose tolerance (Karlsson et al, 2013, Nature 498:99-103; Zeevi et al, 2015, Cell, 163:1079-1094; Yassour et al, 2016, Genome Med, 8:17). Microbe presence was characterized in terms of both diversity and abundance. 16s rRNA and metagenomic sequence data from selected studies were independently analyzed to identify bacterial species which are more likely to be found in the intestine of healthy subjects compared to those more likely to be found in the intestine of subjects suffering.

Bacterial strains identified as potentially significantly associated with healthy individuals were obtained, cultured and analyzed to test their ability to improve physiologic parameters characteristic of metabolic disorders. As described in Example 1, a high fat diet (HFD) induced mouse model was used in which C57BL/6J mice were fed a diet which is about 60% fat and 20% carbohydrates. The HFD fed C57BL/6J mice are susceptible to obesity, type 2 diabetes and atherosclerosis when maintained on this high fat diet (Collins et al., 2004, Physiol Behav, 81:243-248). From these laboratory studies (Example 1), it was determined that administration of *G. sanguinis* results in reduced blood glucose levels when administered to the animals. Moreover, glucose levels were reduced relative to an untreated control in a glucose tolerance test (GTT). Additional analysis was performed to measure changes in mRNA expression of genes associated with lipid oxidation, specifically, ppara (peroxisome proliferator activated receptor alpha), cpt-la (carnitine palmitoyltransferase 1A), and srebf1 (sterol regulatory element binding transcription factor 1), which are markers of lipid oxidation. In each case, treatment of the HFD mice with *G. sanguinis* resulted in a significant decrease in each expression of each gene, consistent with a role in increased fat catabolism.

Another mouse model which may be used to mimic a relevant metabolic disorder is the ob/ob mouse which lacks leptin and eat excessively. As a result, the mouse becomes obese and exhibits other symptoms such as hyperphagia, a diabetes-like syndrome of hyperglycemia, glucose intolerance, elevated plasma insulin, subfertility, impaired wound healing, and an increase in hormone production from both pituitary and adrenal glands.

Accordingly, the data demonstrate that a composition comprising *G. sanguinis* is effective in improving glucose homeostasis and reducing glucose in the blood of a treated subject.

Therapeutically Effective Live Bacteria

A bacterial composition useful for treating a subject suffering from a metabolic disorder may comprise viable *G. sanguinis*, which is further described below.

In some embodiments, the microbes taught herein are identified utilizing 16S rRNA gene sequences. The primary structure of major rRNA subunit 16S comprises a particular combination of conserved, variable, and hypervariable regions that evolve at different rates and enable the resolution of both very ancient lineages such as domains, and more modern lineages such as genera. The secondary structure of the 16S subunit includes approximately 50 helices which result in base pairing of about 67% of the residues. The hypervariable regions can provide species/strain-specific signature sequences useful for bacterial identification. Over the previous few decades, the 16S rRNA gene has become the most sequenced taxonomic marker and is the cornerstone for the current systematic classification of bacteria and archaea (Yarza et al. 2014. *Nature Rev. Micro.* 12:635-645).

Microbes can be distinguished into a genus based on polyphasic taxonomy, which incorporates all available phenotypic and genotypic data into a consensus classification (Vandamme et al., 1996, Microbiol Rev, 60:407-438). In some embodiments, sequence identity of 94.5% or lower for two 16S rRNA genes is strong evidence for distinct genera, 86.5% or lower is strong evidence for distinct families, 82% or lower is strong evidence for distinct orders, 78.5% is strong evidence for distinct classes, and 75% or lower is strong evidence for distinct phyla. Also, populations that share greater than 90%, 91%, 92%, 93%, 94%, 95%, 96%, 97%, 98%, 99%, or 99.9% identity can be considered to be variants of the same species. Another accepted genotypic method for defining species is to isolate marker genes of the present disclosure, sequence these genes, and align these sequenced genes from multiple isolates or variants.

Another accepted genotypic method for defining species is based on overall genomic relatedness, such that strains which share approximately 70% or more relatedness using DNA-DNA hybridization, with 5° C. or less $\Delta T_m$ (the difference in the melting temperature between homologous and heterologous hybrids), under standard conditions, are considered to be members of the same species.

The bacterial strain (*G. sanguinis*) disclosed herein and variants thereof may be characterized in part or in whole by comparing at least one 16S rRNA sequence with a corresponding 16S rRNA sequence of a reference strain genomic sequence. Generally, a bacterial strain genomic sequence will contain multiple copies of 16S rRNA sequences. The 16S rRNA gene sequence has been determined for a large number of strains. GenBank (www.ncbi.nlm.nih.gov/genbank/) has over 20 million deposited sequences, of which over 90,000 are of 16S rRNA genes. Comparison of the bacterial 16S rRNA gene sequence has emerged as a preferred genetic technique and allows for new strains to be identified by comparison of sequences with known bacterial DNA sequences using, e.g., BLAST (blast.ncbi.nlm.nih.gov/Blast.cgi). In short, the comparison of the 16S rRNA sequence allows differentiation between organisms at the genus level across all major phyla of bacteria, in addition to classifying strains at multiple levels, including species and sub-species level.

*Gemella sanguinis* (*G. sanguinis*)

*Gemella sanguinis* was identified after isolation from a blood culture from a 41-year-old male and described by Collins et al. in 1998 (J Clin Microbiol 36:3090-3093). Collins et al. described the strain as gram-positive, non-spore-forming cocci that occur singly, in pairs, or in short chains. *G. sanguinis* is a facultative anaerobe and is catalase and oxidase negative. *G. sanguinis* was deposited into ATCC as deposit No. 700632. Collins et al. also sequenced a 16s rRNA from *G. sanguinis* and deposited the sequence in GenBank under Acc. No. Y13364 (SEQ ID NO:1). Whole genome shotgun sequencing has been performed to determine the genomic sequence for *G. sanguinis*. The resultant genomic sequences are published as GenBank Locus JNJO00000000 (31 contigs deposited as GenBank Acc. Nos. JNJO01000001 to JNJO01000031). Whole genome shotgun sequencing has also been performed for *G. sanguinis* strains M325 (GenBank Locus ACRY02000000; GenBank Acc. Nos. ACRY0200000 to ACRY02000005) and 1094_BTHU (GenBank Acc. No. JWDE01000000; GenBank Acc. Nos. JWDE01000001 to JWDE01000118). Accordingly, the present disclosure is directed to compositions and methods related to *G. sanguinis* or variants thereof, wherein the *G. sanguinis* strain used in the present compositions and methods is identical to ATCC deposit no. 700632, or harbors a genome which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of ATCC deposit no. 700632. Also contemplated are compositions comprising synthetic bacteria that have an engineered genome which has the same therapeutic efficacy as *G. sanguinis* as described herein. In some embodiments, such a microbe has a genome which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of ATCC deposit no. 700632.

Variants of the bacterial strains (*G. sanguinis*) disclosed herein may be characterized by comparing at least one 16S rRNA sequence with a corresponding 16S rRNA sequence of a reference strain genomic sequence. Comparison of the bacterial 16S rRNA gene sequence has emerged as a reliable genetic technique and allows for new strains to be identified by comparison of sequences with known bacterial DNA sequences using, e.g., BLAST (blast.ncbi.nlm.nih.gov/Blast.cgi). The 16S rRNA gene sequence is universal in bacteria, and so relationships can be measured across many different bacteria. In general, the comparison of the 16S rRNA sequence allows differentiation between organisms at the genus level across all major phyla of bacteria, in addition to classifying strains at multiple levels, including species and sub-species level. The 16S rRNA gene sequence has been determined for a large number of strains. GenBank, the largest databank of nucleotide sequences, has over 20 million deposited sequences, of which over 90,000 are of 16S rRNA genes.

Generally, a bacterial strain genomic sequence will contain multiple copies of 16S rRNA sequences. The 16S rRNA sequences are often used for making distinctions between species and strains, in that if one or more of the aforementioned sequences shares less than a specified % sequence identity from a reference sequence, then the two organisms from which the sequences were obtained are said to be of different species or strains.

A 16S rRNA sequence of ATCC deposit no. 700641 can be found at GenBank Accession No. Y13364 (SEQ ID NO:1). In some embodiments, a composition according to the present disclosure comprises an *G. sanguinis* bacterium wherein its genome comprises one or more 16S rRNA-encoding sequences that are at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to the 16S rRNA sequence of GenBank Acc. No. Y13364 (SEQ ID NO:1).

The disclosure also encompasses the use of variants of the bacterial species or strains described herein including those obtained by genetic engineering techniques to alter the genetic material of the strains of the disclosure or recombining the genetic material of the strains of the disclosure with other polynucleotides. In order to obtain such variant strains, a person skilled in the art can use standard mutagenesis techniques, such as UV radiation or exposure to mutagenic chemical products. The disclosure further comprises any microbes harboring a synthetically derived genome that shares the aforementioned sequence identity to the sequence of GenBank accession number JNJO00000000. Thus, the disclosure includes naturally isolated, recombinantly produced, and synthetically derived microbes.

In some embodiments, the variants include mutants or derived bacterial strains having a genomic sequence which is at least 90%, 91%, 92%, 93%, 94%, 95%, 96%, 97%, 98%, 99%, 99.5%, 99.9%, 99.99% or 99.999% identical to the polynucleotide sequence of a referenced strain (e.g., *G. sanguinis* GenBank Acc. No. JNJO00000000). Examples of software that can perform sequence comparisons include, but are not limited to, the BLAST package (see Ausubel, et al. 1999 Short Protocols in Molecular Biology, 4th Ed-Chapter 18), BLAST 2 (see FEMS Microbial Lett 1999 174(2): 247-50; FEMS Microbial Lett 1999 177(1): 187-8), FASTA (Altschul, et al. 1990 J Mol Biol 403-410) and AlignX for example.

Accordingly, a microbe of the disclosure comprises a genomic sequence that is at least 90%, 91%, 92%, 93%, 94%, 95%, 96%, 97%, 98%, 99%, 99.5%, 99.9%, 99.99% or 99.999% identical to the sequence depicted in GenBank accession number JNJO00000000, and also has the functional ability to improve the health of a subject in need thereof as described in more detail below.

In some embodiments, a microbe of the disclosure comprises a genomic sequence that is at least 90%, 91%, 92%, 93%, 94%, 95%, 96%, 97%, 98%, 99%, 99.5%, 99.9%, 99.99% or 99.999% identical to the sequence depicted in GenBank accession number JNJO00000000, and also has the functional ability to reduce blood glucose levels, reduce intestinal epithelial barrier permeability (i.e., increase gastrointestinal epithelial cell barrier function in a subject (or in an in vitro cellular assay), and/or reduce pro-inflammatory cytokines when administered to a subject.

In some embodiments, a microbe of the disclosure comprises a genomic sequence that is at least 90%, 91%, 92%, 93%, 94%, 95%, 96%, 97%, 98%, 99%, 99.5%, 99.9%, 99.99% or 99.999% identical to the sequence depicted in GenBank accession number JNJO00000000, and also has the functional ability to improve at least one side effect, or ameliorate at least one symptom, or improve and/or regulate glucose homeostasis and/or glycemic control, when administered to a patient in need thereof.

Therapeutic Uses for *G. sanguinis*

An increasing number of studies show that a subject's microbiome can affect or be associated with predisposition to or incidence of a metabolic disorder (for a review, see, e.g., Eid et al., 2017, Front Pharmacol, 8: article 387; Johnson et al., 2017, J Mol Med, 95:1-8; Yang and Kweon, 2016, BMB Rep, 49:536-541). Provided herein are methods for treating a metabolic disorder by administering to a subject suffering from the metabolic disorder a composition that contains *G. sanguinis* as viable bacteria. The Examples provided below show that administration of these bacteria can reduce blood glucose levels as well as increase glucose tolerance in an animal. This improvement in glucose homeostasis shows that the composition is useful in the treatment of numerous metabolic diseases or disorders as such diseases and disorders are linked to dysfunctional glucose homeostasis. Such metabolic diseases and disorders which can be treated with the compositions comprising *G. sanguinis* as disclosed herein are described in more detail below. It thereby follows that the compositions comprising *G. sanguinis* as disclosed herein are further able to reduce, ameliorate or reverse one or more symptoms of these diseases and disorders.

Accordingly, methods are provided for treating, preventing, or ameliorating at least one symptom of a disease or condition, including: administering a therapeutically or prophylactically effective amount of microbe(s) as described herein to a subject in need thereof, i.e., a subject suffering from, or at risk of developing the disease or condition, or at least one symptom of the disease or condition.

Metabolic syndrome is a term used to refer to a cluster of conditions including increased blood pressure, high blood sugar (hyperglycemia), obesity including excess body fat around the waist, and abnormal cholesterol or triglyceride levels. These conditions tend to occur together and can increase risk of heart disease, stroke and diabetes. Any one of the conditions can indicate a predisposition to a serious disease such as type 2 diabetes or atherosclerosis.

Hyperglycemia, the condition of high blood glucose levels, is a hallmark of altered metabolism. The effects of hyperglycemia are disastrous on multiple levels, as it disrupts a number of crucial processes at the cellular level, as well as having adverse effects in a tissue-specific manner (e.g. blindness of eye), on whole organs (e.g. kidney disease), and even including systemic host effects (e.g. ketoacidosis, coma, death, etc.) manner.

Subjects who suffer from or are predisposed to T2DM and/or obesity can present with fasting glucose levels that are higher than normal, e.g., greater than about 125 mg/dL or 130 mg/dL (see, e.g., Pippitt et al., 2016, Amer Fam Physic, 93:103-109). The fasting glucose level is a measurement of blood glucose in a subject who has not eaten for at least 8 hours. Subjects who may benefit from therapy with *G. sanguinis*, include those who have been determined to have a fasting blood glucose level greater than about 125 mg/dL, 130 mg/dL, 140 mg/dL, 150 mg/dL, 160 mg/dL, 170 mg/dL, 180 mg/dL, 190 mg/dL or 200 mg/dL. Accordingly, envisioned herein are methods to reduce hyperglycemia or glucose blood levels in a subject in need thereof, wherein administration of a composition comprising *G. sanguinis* reduces the fasting glucose level in the subject to a level below 125 mg/dL, below 130 mg/dL, below 140 mg/dL, or below 150 mg/dL.

These subjects can also have impaired glucose tolerance, e.g., a two-hour plasma glucose in a 75 g oral glucose tolerance test of about 140-199 mg/dL (7.8 to 11.0 mmol per L). The determination of fasting blood glucose level may have been performed 1-7 days or 1-4 weeks prior to the first administration of a composition comprising *G. sanguinis* to the subject. Subjects who may benefit from therapy with *G. sanguinis* include those who have been determined to have a 2-hour value for a 75 gram oral glucose tolerance test (OGTT) of greater than about 140 mg/dL, 150 mg/dL, 160 mg/dL, 170 mg/dL, 180 mg/dL, 190 mg/dL or 200 mg/dL.

Alternatively, a subject suffering from hyperglycemia can have postprandial or reactive hyperglycemia which occurs after eating. Postprandial or reactive hyperglycemia is a blood glucose level above about 180 mg/dL at a time 1-2 hours after eating. Accordingly, envisioned herein are methods to reduce hyperglycemia or glucose blood levels in a subject in need thereof, wherein administration of a composition comprising *G. sanguinis* reduces the postprandial blood glucose to a level below 180 mg/dL, below 190 mg/dL, below 200 mg/dL, or below 210 mg/dL, when measure 1 or 2 hours after eating.

Symptoms of hyperglycemia can be headaches, increased urination, thirst, nausea, blurred vision, weight loss, fatigue, and coma. Hyperglycemia can be caused by hypoinsulinism, a condition in which the insulin producing β cells of the pancreas fail to manufacture insulin or manufacture and secrete a reduced amount of insulin into the bloodstream. In such cases, levels of sugar in the blood are dramatically increased resulting in hyperglycemia. Hyperglycemia can also be caused by failure of some or all of the available insulin in the blood to bind to the body's cell receptors and/or internalization of insulin in the cells is reduced. Accordingly, provided herein are methods to reduce, ameliorate or reverse one or more symptoms of hyperglycemia.

Diabetes mellitus is a metabolic, chemical disorder of the human body primarily involving an inability of the body to properly utilize sugar, i.e. glucose, and other chemical compounds involved in the metabolism of the body. It is characterized by an elevation in the concentration of sugar in the blood and by the appearance of sugar in the urine. It is estimated that 1.5 to 2% of the world population suffers from diabetes mellitus of some type. In general terms, diabetes mellitus is classified into three main types, namely, type 1 diabetes, impaired glucose tolerance (IGT) and type 2 diabetes (T2DM). In most cases of type 1 diabetes, the β cells in the pancreas, probably through an autoimmune reaction, cease producing insulin into the bloodstream of the person. Insulin is vitally important because it enables properly utilization and consumption of sugar in the bloodstream as part of the metabolism process.

In impaired glucose tolerance and T2DM, the pancreas continues to produce insulin, but the insulin may fail to bind to the appropriate cell receptors and/or internalization of insulin in the cells is reduced. In such cases, there may be a sufficient level of insulin in the blood, but the ability of the cells to uptake glucose is reduced or non-existent because of reduced internalized insulin.

T2DM is one of the most common causes of hyperglycemia. The large-scale DCCT study (See The Diabetes Control and Complications Trial Research Group (1993) N. Engl. J. Med. 329, 977-986) concluded that chronically increased levels of blood glucose are a main reason underlying the development of complications in a number of diabetes conditions. It could clearly be shown by the DCCT study in the USA that chronically increased levels of blood glucose are a main reason for the development of diabetes complications, leading to a decreased life expectancy. Cardiovascular deaths with a risk of coronary heart disease increased by 2- to 4-fold in this population, as one example. Examples for diabetes complications include, but are not limited to, micro- and macrovascular damages that possibly manifest themselves in retinopathies, nephropathies that may or may not lead to blindness, renal failure, and the loss of extremities, and are accompanied by an increased risk of cardiovascular diseases.

Figure 2:
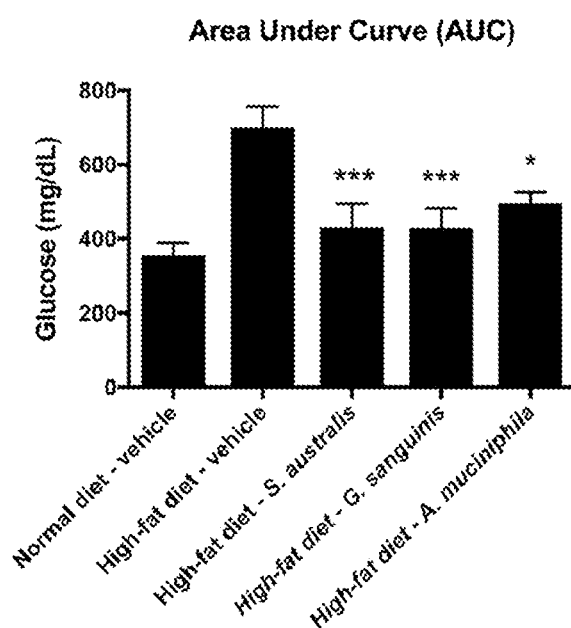
FIG. 2 shows effects of treatment with *G. sanguinis* on glucose homeostasis by presenting Area under the curve (AUC) from normalized GTT (FIG. 1) in a high-fat diet-induced obese mouse, as described in Example 1.

The existence of type 1, IGT, or type 2 diabetes in a person is usually determined by an oral glucose tolerance test (OGTT). OGTT is a test in which the fasting individual is given a known amount of glucose (sugar) by mouth, and the blood is tested at intervals thereafter to note the quantity of sugar in the blood. A curve is then constructed from which important information about the individual can be drawn. The glucose tolerance test curve will typically show whether the individual is hyperglycemic (diabetic) or whether the individual has too little sugar in his or her blood and is therefore hypoglycemic. Example 1 below shows that administration of *G. sanguinis* to HFD mouse increased glucose tolerance as seen by the decrease in glucose AUC (area under the curve) (FIG. 2). It is further noted that treatment with *G. sanguinis* resulted in a decrease in subcutaneous fat (FIG. 3B) without a similar effect on body weight (FIGS. 4A and 4B) suggesting that the observed loss of subcutaneous was likely accompanied by a corresponding weight gain in muscle mass and/or bone density.

In view of these beneficial effects of *G. sanguinis* administration to reduce glucose levels in the blood of a subject and to increase glucose tolerance (and homeostasis), provided herein are compositions comprising *G. sanguinis* and use of these compositions to treat a subject suffering from hyperglycemia, hyperinsulinaemia, hyperlipidaemia, insulin resistance, insulin insensitivity, impaired glucose metabolism, impaired glucose tolerance, type 2 diabetes mellitus, obesity, diabetic retinopathy, macular degeneration, foot ulcerations, metabolic acidosis, cataracts, diabetic nephropathy, glomerulosclerosis, diabetic neuropathy, erectile dysfunction, premenstrual syndrome, vascular restenosis, coronary heart disease, hypertension, angina pectoris, myocardial infarction, stroke, skin and connective tissue disorders, arthritis, osteoporosis, and combinations thereof. Also provided are methods for decreasing, ameliorating, and/or reversing one or more symptoms of any of the above-listed disorders. Such symptoms include, for example, headaches, blurred vision, increased urination, thirst, nausea, weight loss, fatigue, and coma.

It is understood that the subject can be a human, a non-human primate or other animal, including but not limited to pets such as dogs and cats, livestock such as cows, horses, pigs, goats, rabbits, and other animals such as rodents (mice and rats), or any other animal in need thereof.

Dysbiosis is also known to have a detrimental effect on other physiologies such as inflammation and immunity. Accordingly, it is highly likely that beneficial effects of therapy using probiotics or live biotherapeutic products will extend beyond a single disorder. For example, administration of a composition comprising *G. sanguinis* to treat symptoms related to a metabolic disorder may also have beneficial effects on other disorders such as inflammatory disorders including inflammatory bowels diseases such as Crohn's disease or ulcerative colitis.

One means for testing the efficacy of a composition according to the present disclosure as effective in treating an IBD is an in vitro assay of intestinal epithelial barrier disease. Gastrointestinal epithelial barrier integrity can be measured in in vitro experimental systems using a transepithelial/transendothelial electrical resistance (TEER) assay which measures electrical resistance across a cellular monolayer. This very sensitive and reliable method determines integrity and permeability of the monolayer. Background information on TEER assays is available, e.g., in Dewi, et al. (2004) *J. Virol. Methods.* 121:171-180, and in Mandic, et al. (2004) *Clin. Exp. Metast.* 21:699-704. Guidance on transendothelial cell albumin permeability assays is available, e.g., in Dewi, et al. (2008) *J. Gen. Virol.* 89:642-652. Staurosporine is a reagent that can be used as a control with TEER assays. Accordingly, in some embodiments, a method is provided for increasing intestinal epithelial barrier function integrity with a composition comprising *G. sanguinis*, wherein the method increases electrical resistance in a TEER assay by at least 10%, 20%, 30%, 40%, 50%, 60%, 70%, 80%, 90% or 100% as compared to the TEER assay run in the absence of *G. sanguinis*.

Therapeutic efficacy of the compositions and methods disclosed herein can encompass a reduction in symptoms associated with the indication being treated. For example, a subject diagnosed with and being treated for type 2 diabetes, may see a reduction is one or more symptoms selected from the group consisting of dry mouth and itchy skin, blurred vision, onset of a yeast infection and pain or numbness in the feet or legs. A reduction in symptoms can be a reduction in the number of times a subject experiences the symptom(s) in a 24-hour period. The reduction in the one or more symptoms can be observed over, e.g., a period of about 1-2 months, 1-5 months, or 6-12 months after the initiation of treatment.

Compositions Comprising *G. sanguinis*

The microbe compositions of the present disclosure can be administered to a subject in need thereof to enhance general health and well-being and/or to treat or prevent a disease or disorder such as a metabolic disorder or disorder associated with reduced intestinal epithelial barrier function as described herein. In some embodiments, the microbe composition is a live biotherapeutic product (LBP) while in other embodiments, the microbe composition is a probiotic. In some embodiments, the *G. sanguinis* is isolated and has been cultured outside of a subject to increase the number or concentration of the microbes, thereby enhancing the therapeutic efficacy of a composition comprising the microbe population.

In some embodiments, the microbe composition is in the form of a live bacterial population. The live population may be, e.g., frozen, cryoprotected or lyophilized. In other embodiments, the microbe composition comprises a non-viable bacterial preparation, or the cellular components thereof. In some embodiments, where the microbe composition is in the form of a non-viable bacterial preparation, it is selected from, for example, heat-killed bacteria, irradiated bacteria and lysed bacteria.

In some embodiments, the bacterial species is in biologically pure form, substantially free from other species of organism. In some embodiments, the bacterial species is in the form of a culture of a single species of organism.

Compositions comprising *G. sanguinis* in accordance with the present disclosure can be any of a number of accepted probiotic or live biotherapeutic product (LBP) delivery systems suitable for administration to a subject. Importantly, a composition for delivery of a live population of *G. sanguinis* must be formulated to maintain viability of the microbe. In some embodiments, the composition comprises elements which protect the bacteria from the acidic environment of the stomach. In some embodiments, the composition includes an enteric coating.

In some embodiments, the composition is a food-based product. A food-based product can be, for example, a yogurt, cheese, milk, meat, cream, or chocolate. Such food-based products can be considered edible, which means that it is approved for human or animal consumption.

One aspect of the disclosure relates to a food product comprising the bacterial species defined above. The term "food product" is intended to cover all consumable products that can be solid, jellied or liquid. Suitable food products may include, for example, functional food products, food compositions, pet food, livestock feed, health foods, feedstuffs, and the like. In some embodiments, the food product is a prescribed health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present disclosure include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for humans, pets, or livestock.

In one embodiment, the composition according to the present disclosure is a food product intended for humans, pets or livestock. The composition may be intended for animals selected from the group consisting of non-human primates, dogs, cats, pigs, cattle, horses, goats, sheep, or poultry. In another embodiment, the composition is a food product intended for adult species, in particular human adults.

Another aspect of the disclosure relates to food products, dietary supplements, nutraceuticals, nutritional formulae, drinks and medicaments containing the bacterial species as defined above, and use thereof.

In the present disclosure, "milk-based product" means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavored milks, ice cream; milk-containing food such as sweets.

The microbe composition can be a tablet, a chewable tablet, a capsule, a stick pack, a powder, or effervescent powder. The composition can comprise coated beads which contain the bacteria. A powder may be suspended or dissolved in a drinkable liquid such as water for administration.

In some embodiments, the microbe composition comprises a microbe which is isolated. The isolated microbe may be included in a composition with one or more additional substance(s). For example, the isolated microbe may be included in a pharmaceutical composition with one or more pharmaceutically acceptable excipient(s).

In some embodiments, the microbe composition may be used to promote or improve human health. In some aspects, the microbe composition may be used to improve gut health. In some aspects, the microbe composition may be used to regulate appetite. In some aspects, the microbe composition may be used to regulate blood glucose levels. In some aspects, the microbe composition may be used to regulate insulin sensitivity. In some embodiments, the disclosed microbe composition is used for regulating appetite in a subject.

The microbes described herein may also be used in prophylactic applications. In prophylactic applications, bacterial species or compositions according to the disclosure are administered to a patient susceptible to, or otherwise at risk of, a particular disease in an amount that is sufficient to at least partially reduce the risk of developing a disease. The precise amounts depend on a number of patient specific factors such as the patient's state of health and weight.

In some embodiments, the disclosure provides for various immediate and controlled release formulations comprising the taught microbes and combinations thereof. Controlled release formulations sometimes involve a controlled release coating disposed over the bacteria. In particular embodiments, the controlled release coatings may be enteric coatings, semi-enteric coatings, delayed release coatings, or pulsed release coatings may be desired. In particular, a coating will be suitable if it provides an appropriate lag in active release (i.e. release of the therapeutic microbes and combinations thereof). It can be appreciated that in some embodiments one does not desire the therapeutic microbes and combinations thereof to be released into the acidic environment of the stomach, which could potentially degrade and/or destroy the taught microbes, before it reaches a desired target in the intestines.

In some embodiments, the microbe compositions of this disclosure encompass *G. sanguinis* and any variants thereof as described above.

In some embodiments, the microbe composition of the present disclosure further comprises a prebiotic in an amount of from about 1 to about 30% by weight, respect to the total weight composition, preferably from 5 to 20% by weight. Preferred carbohydrates are selected from: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. Particularly preferred prebiotics are the short-chain fructo-oligosaccharides (for simplicity shown herein below as FOSs-c.c); said FOSs-c.c. are not digestible carbohydrates, generally obtained by the conversion of the beet sugar and containing a saccharose molecule to which three glucose molecules are bonded.

In one embodiment, the composition further comprises at least one other kind of other food grade bacterium, wherein the food grade bacterium is preferably selected from the group consisting of lactic acid bacteria, bifidobacteria, propionibacteria or mixtures thereof.

In some embodiments, microbe compositions comprise $10^6$-$10^{12}$ CFU (colony forming units), $10^8$-$10^{12}$ CFU, $10^{10}$-$10^{12}$ CFU, $10^8$-$10^{10}$ CFU, or $10^8$-$10^{11}$ CFU of *G. sanguinis*. In other embodiments, microbial combinations comprise about $10^6$, about $10^7$, about $10^8$, about $10^9$, about $10^{10}$, about $10^{11}$, or about $10^{12}$ CFU of *G. sanguinis*.

A composition comprising *G. sanguinis* according to the present disclosure can be formulated for delivery to a desired site of action within an individual to whom it is administered. For example, the composition may be formulated for oral and/or rectal administration. Additionally, the composition may be formulation for administration to the gastrointestinal lumen, or for delayed release in the intestine, terminal ileum, or colon.

When employed as a pharmaceutical, i.e., for treatment or prophylaxis of a disease, disorder, or condition, the compositions described herein are typically administered in the form of a pharmaceutical composition. Such compositions can be prepared in a manner well known in the pharmaceutical art and include at least one active compound, i.e., a live strain as described herein. Generally, the compositions are administered in a pharmaceutically effective amount, i.e., a therapeutically or prophylactically effective amount. The amount of the active agent, i.e., a microbe as described herein, administered will typically be determined by a physician, in the light of the relevant circumstances, including the condition to be treated, the chosen route of administration, the activity of the microbe or microbes administered, the age, weight, and response of the individual patient, the severity of the patient's symptoms, and the like.

The compositions can be administered by a variety of routes including oral, rectal, and intranasal. Depending on the intended route of delivery, the compositions are formulated as either injectable or oral compositions, or as salves, as lotions, or as patches.

The compositions for oral administration can take the form of bulk liquid solutions or suspensions, or bulk powders. More commonly, however, the compositions are presented in unit dosage forms to facilitate accurate dosing. Typical unit dosage forms include prefilled, premeasured ampules or syringes of the liquid compositions or pills, tablets, capsules or the like in the case of solid compositions. The above-described components for orally administrable, or injectable administrable compositions are merely representative. Other materials, as well as processing techniques and the like are set forth in Part 8 of Remington's The Science and Practice of Pharmacy, 21$^{st}$ edition, 2005, Publisher: Lippincott Williams & Wilkins, which is incorporated herein by reference.

For oral administration, particular use is made of compressed tablets, pills, tablets, gellules, drops, and capsules.

The compositions may be formulated in unit dosage form, i.e., in the form of discrete portions containing a unit dose, or a multiple or sub-unit of a unit dose.

In another embodiment, the compositions of the disclosure are administered in combination with one or more other active agents. In such cases, the compositions of the disclosure may be administered consecutively, simultaneously or sequentially with the one or more other active agents.

Dosage and Administration Schedule

The dosages disclosed herein are exemplary of the average case. There can of course be individual instances where higher or lower dosage ranges are merited, and such are within the scope of this disclosure. The term "unit dosage form" refers to a physically discrete unit suitable as a unitary dosage for an individual to whom administered, each unit containing a predetermined quantity of active material calculated to produce the desired therapeutic or prophylactic effect, and may be in association with a suitable pharmaceutical excipient.

In some embodiments, the effective daily dose in a subject is from about $1\times10^6$ to about $1\times10^{12}$ colony forming units (CFUs), $1\times10^7$ to $1\times10^{12}$ CFUs, $1\times10^8$ to $1\times10^{12}$ CFUs, $1\times10^8$ to $1\times10^{11}$ CFUs, $1\times10^8$ to $1\times10^{10}$ CFUs, $1\times10^8$ to $1\times10^9$ CFUs, $1\times10^9$ to $1\times10^{12}$ CFUs, $1\times10^{10}$ to $1\times10^{12}$ CFUs, or $1\times10^{10}$ to $1\times10^{11}$ CFUs. The subject may be a human or non-human primate. Alternatively, the subject may be another mammal such as a rat, mouse, rabbit, etc.

In some embodiments, the daily dose is administered to the subject daily for about 1 to 2 weeks, 1 to 4 weeks, 1 to 2 months, 1 to 6 months, 1 to 12 months.

Alternatively, the dose which ranges from about $1\times10^6$ to about $1\times10^{12}$ colony forming units (CFUs), $1\times10^7$ to $1\times10^{12}$ CFUs, $1\times10^8$ to $1\times10^{12}$ CFUs, $1\times10^8$ to $1\times10^{11}$ CFUs, $1\times10^8$ to $1\times10^{10}$ CFUs, $1\times10^8$ to $1\times10^9$ CFUs, $1\times10^9$ to $1\times10^{12}$ CFUs, $1\times10^{10}$ to $1\times10^{12}$ CFUs, or $1\times10^{10}$ to $1\times10^{11}$ CFUs is administered to a subject every other day, once per week, 3 times per week, 5 times per week, once per month, twice per month, 3 times per month, once every 2 months, or 3 times, 4 times or 6 times per year. In these embodiments, the dose can be administered to the subject for a period extending from about 1 to 2 weeks, 1 to 4 weeks, 1 to 2 months, 1 to 6 months, 1 to 12 months.

The dose administered to a subject should be sufficient to treat a disease and/or condition, partially reverse a disease and/or condition, fully reverse a disease and/or condition, or establish a healthy-state microbiome. In some aspects, the dose administered to a subject should be sufficient to prevent the onset of symptoms associated with a metabolic disorder, such as hyperglycemia, type 2 diabetes, or obesity. In other embodiments, the dose is effective to treat or ameliorate the symptoms of an inflammatory disorder. In some embodiments, the inflammatory is an inflammatory bowel disease such as Crohn's disease or ulcerative colitis.

Dosing may be in one or a combination of two or more administrations, e.g., daily, bi-daily, weekly, monthly, or otherwise in accordance with the judgment of the clinician or practitioner, taking into account factors such as age, weight, severity of the disease, and the dose administered in each administration.

In another embodiment, an effective amount can be provided in from 1 to 500 ml or from 1 to 500 grams of the bacterial composition having from $10^7$ to $10^{11}$ bacteria per ml or per gram, or a capsule, tablet or suppository having from 1 mg to 1000 mg lyophilized powder having from $10^7$ to $10^{11}$ bacteria. Those receiving acute treatment can receive higher doses than those who are receiving chronic administration (such as hospital workers or those admitted into long-term care facilities).

The effective dose as described above, can be administered, for example, orally, rectally, intravenously, via a subcutaneous injection, or transdermally. The effective dose can be provided as a solid or liquid, and can be present in one or more dosage form units (e.g., tablets or capsules).

Combination Therapies

The compositions taught herein comprising a therapeutic microbe may be combined with other treatment therapies and/or pharmaceutical compositions. For example, a patient suffering from a metabolic syndrome or disorder such as hyperglycemia, obesity or type 2 diabetes may already be taking a pharmaceutical prescribed by their doctor to treat the condition. In embodiments, the compositions taught herein, are able to be administered in conjunction with the patient's existing medicines.

The compositions, with or without one or more prebiotics, can be administered with other agents in a combination therapy mode, including anti-microbial agents. Administration can be sequential, over a period of hours or days, or simultaneous.

In one embodiment, the microbial compositions, with or without one or more prebiotics, are included in combination therapy with one or more anti-microbial agents, which include anti-bacterial agents, anti-fungal agents, anti-viral agents, and anti-parasitic agents. In some embodiments, the anti-microbial agent(s) does not kill or inhibit function or growth of *G. sanguinis*.

Patient Selection Based on Microbiome

In some embodiments, subjects are human. In other embodiments, subjects are other animals, including but not limited to non-human primates, pigs, goats, dogs, cows, horses, chickens, mice, rats, and cats.

In addition to identifying subjects that may benefit from therapy comprising administration of *G. sanguinis* by determining, e.g., blood glucose levels, glucose tolerance, and/or BMI, a subject may be identified according to the profile of their gut microbiome. Particular bacterial compositions can be selected for individual subjects or for subjects with particular profiles. For example, 16S rRNA sequencing can be performed for a given subject to identify the bacteria present in his or her microbiota. The 16S rRNA sequencing can be used with other methods, e.g., microprofiling, for determining a subject's microbiome profile. The sequencing can either profile the subject's entire microbiome using 16S sequencing (to the family, genera, or species level), a portion of the subject's microbiome using 16S sequencing, or it can be used to detect the presence or absence of specific candidate bacteria that are biomarkers for health or a particular disease state, such as markers of multi-drug resistant organisms or specific genera of concern. Based on the biomarker data, a particular composition can be selected for administration to a subject to supplement or complement a subject's microbiota in order to restore health or treat or prevent disease. In another embodiment, subjects can be screened to determine the composition of their micro biota to determine the likelihood of successful treatment.

Kits

In certain aspects, the disclosure relates to kits for the treatment of a metabolic or inflammatory disorder or disease. The kits comprise a microbial composition according to the present disclosure. In some embodiments, the kit further comprises a prebiotic, a second therapeutic agent as described herein, or a combination thereof.

The kits provided may comprise one or more containers. The containers may comprise singly isolated microbial compositions comprising one or more microbes and/or singly isolated prebiotic compositions comprising one or more carbohydrates. The microbial compositions, with or without one or more prebiotics, in the different containers may be administered at the same time or at different times, and may be administered in a specific order.

The microbial composition, with or without one or more prebiotics, may comprise live microbes, microbes that are lyophilized, freeze-dried, and/or substantially dehydrated, or the composition may comprise bacterial spores.

The following examples are intended to illustrate, but not limit, the disclosure.

Examples

The following experiments utilize a robust mixture of in vivo experiments utilizing animal models of obesity/diabetes to demonstrate the therapeutic ability of the taught microbes, alone and in combination, and methods thereof. A commonly used animal model to mimic human obesity, hyperglycemia, type 2 diabetes, and associated conditions and diseases is the use of the ob/ob mouse model (see, e.g., Lindström, P. (2007) *Scientific World Journal.* 7: 666-685 for review). In addition, a high fat diet-induced mouse model can be used such as C57BL/6J mice that are fed a diet which is about 60% fat and 20% carbohydrates (Collins et al., 2004, Physiol Behav, 81:243-248).

The following experiments utilize a robust mixture of in vivo experiments utilizing models of obesity/diabetes to demonstrate the therapeutic ability of the taught microbes, alone and in combination, and methods thereof.

Example 1

Effects of *Gemella sanguinis* (*G. sanguinis*) on Glucose Homeostasis

This example studies the effects of administering live *G. sanguinis* bacteria to a high-fat diet-induced obese mouse model. A set of C57BL/6J background mice (The Jackson Laboratory) were housed in groups of 5 per cage, with free access to food and water. The mice were fed either a control diet (18% protein and 6% fat, Teklad global T2018) or a high fat diet (60% fat and 20% carbohydrates, Research Diets D12492).

A total of 10 mice were fed a normal (control) diet. 40 mice, who were fed a high-fat diet, were split into 4 groups for the following treatments: vehicle only, composition comprising *S. australis*, composition comprising *Gemella sanguinis* (*G. sanguinis*), or Akkermansia muciniphila (*A. muciniphila*). ATCC Deposit numbers from strains used are: *Streptococcus australis* (ATCC 700641), *Gemella sanguinis* (ATCC 700632), and Akkermansia muciniphila (ATCC BAA-835). Before the treatment, all mice were administered 100 µL of 10% sodium bicarbonate by oral gavage. The vehicle only treatment was by oral gavage, in which 100 µL sterile PBS was administered. For treatment with microbial compositions, 100 µL sterile PBS containing $2 \times 10^8$ colony forming units (CFU) of *S. australis*, *G. sanguinis*, or *A. muciniphila* was administered via oral gavage once per day for 4 weeks (28 days).

This example studies the effects of administering live bacteria on glucose homeostasis by performing glucose tolerance tests (GTTs) on the high-fat diet-induced obese mouse model. The mice prepared and used for Example 1 were the same mice as used in this study.

On Day 27, prior to sacrificing the mice, the mice were fasted for 4 hr, then injected i.p. with dextrose (1 g/Kg, Hospira, Inc). Glucose excursion following injection was monitored. Blood samples were drawn at 0, 10, 30, 60 and 120 minutes after dextrose injection. Glucose was measured using a One-touch glucose-monitoring system (Lifescan) and normalized blood glucose levels are presented in FIG. 1. Area under the curve (AUC) from normalized GTT (FIG. 2) was determined using GraphPad Prism (*$p<0.05$; ***$p<0.001$ by one-way ANOVA). AUC determines the glucose excursions by measuring the area below the glucose levels over time. It is an arbitrary unit but has units of concentration times time. For example, mg·hr/L or mg·hr·L$^-$$_1$. AUC is used extensively in the calculation drug product performance, that is, dosage form bioavailability.

Treatment with *G. sanguinis*, *S. australis*, and *A. muciniphila* led to an increase in glucose tolerance as measured by decreased blood glucose levels. FIG. 1 shows that treatment with *G. sanguinis*, *S. australis*, and *A. muciniphila* leads to a more rapid reduction in blood glucose levels after glucose administration as compared to treatment with vehicle alone. Moreover, after 30 and 60 minutes, circulating glucose levels were significantly lower in microbe-treated mice compared to the vehicle group. The AUC was accordingly significantly decreased compared to vehicle-treated mice (see FIG. 2).

Example 2

Effects of *G. sanguinis* on Body Weight

Figure 4A:
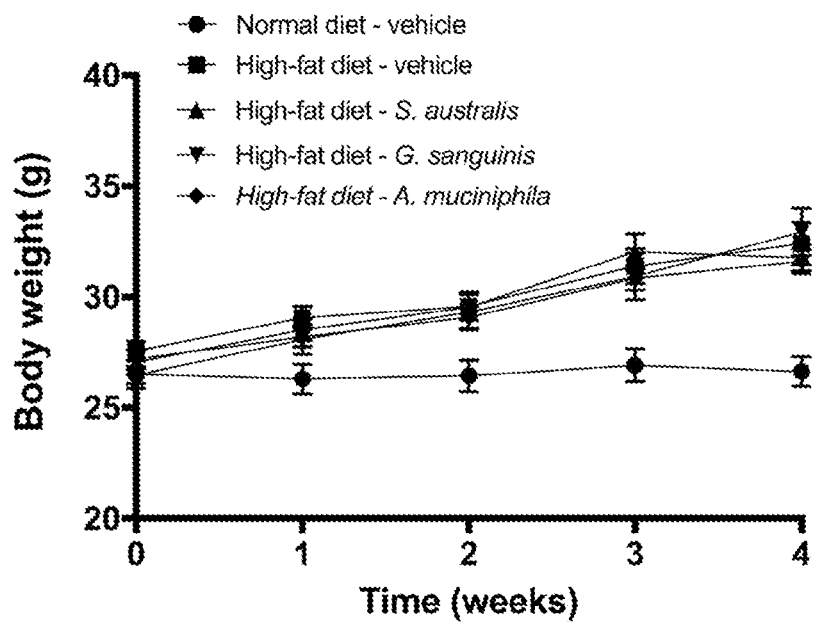
FIG. 4A and FIG. 4B show effects of treatment with *G. sanguinis* on body weight in a high-fat diet-induced obese mouse, as described in Example 2.
Figure 4B:
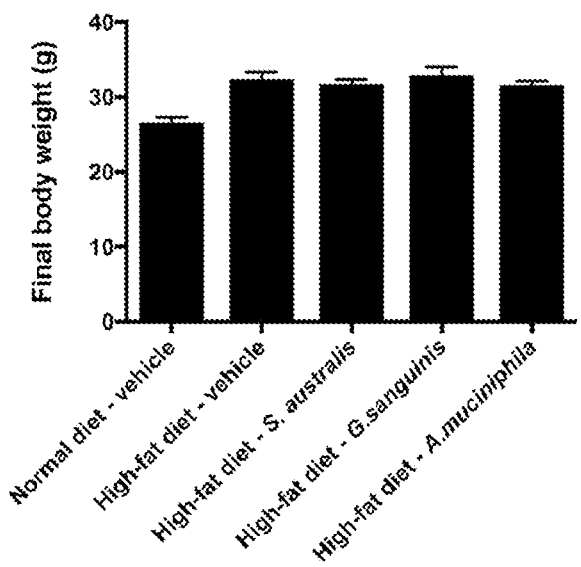

The mice were also analyzed with respect to body weight and fat composition. Total body weight was monitored over the course of the experiment. Also, after sacrifice of the mice on Day 28, each mouse was weighed to determine the final total body weight. As shown in FIG. 4A and FIG. 4B, while mice treated with *S. australis* or with *A. muciniphila* experienced a modest decrease in total body weight as compared to RFD-induced obese mice treated with vehicle only, mice treated with *G. sanguinis* showed no significant change in total body weight.

Figure 3A:
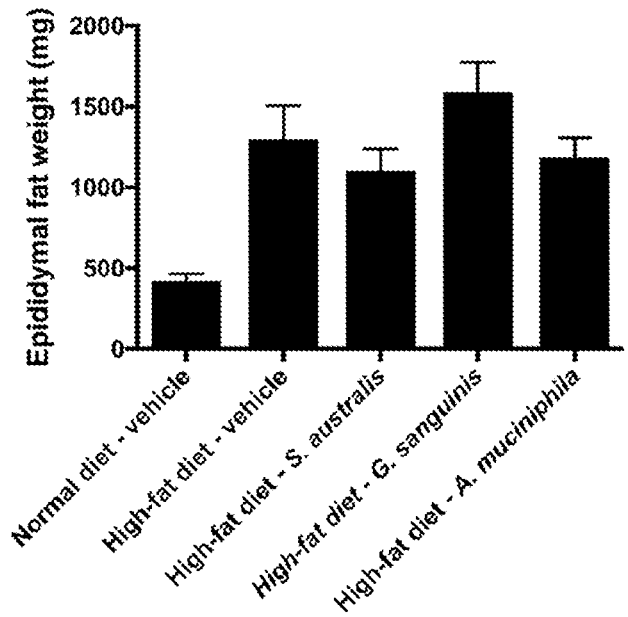
FIG. 3A and FIG. 3B show effects of treatment with *G. sanguinis* on the epididymal (FIG. 3A) and subcutaneous (FIG. 3B) fat weight in a high-fat diet-induced obese mouse, as described in Example 2.
Figure 3B:
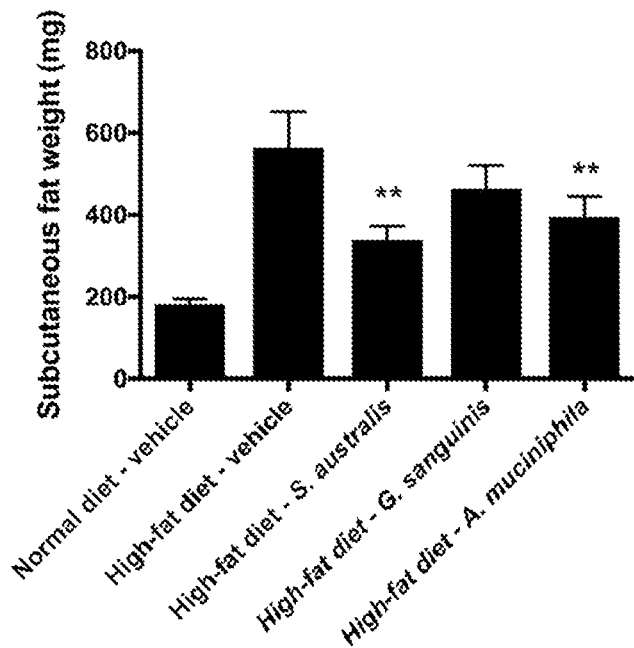

In addition, epididymal and subcutaneous fat were collected separately and weighed for each mouse. As shown in FIG. 3A, there was a moderate decrease in epididymal fat weight in mice treated with *A. muciniphila* as compared to mice treated with vehicle only, however, there was no decrease in epididymal fat weight in mice treated with *G. sanguinis*. With respect to subcutaneous fast, there was a significant decrease in subcutaneous fat for animals treated with *A. muciniphila* in addition to a drastic decrease in subcutaneous fat for animals treated with *G. sanguinis* (FIG. 4B, **$p<0.01$ by one-way ANOVA).

Treatment with *G. sanguinis* resulting in a decrease in subcutaneous fat (FIG. 3B) without a similar effect on body weight (FIGS. 4A and 4B) suggests that the observed loss of subcutaneous was likely accompanied by a corresponding weight gain in muscle mass and/or bone density. Accordingly, the data are consistent with a therapeutic effect of live *G. sanguinis* for addressing metabolic disorders such as obesity, and possibly related disorders such as type 2 diabetes.

Example 3

Effects of *G. sanguinis* on Gene Expression

Figure 5A:
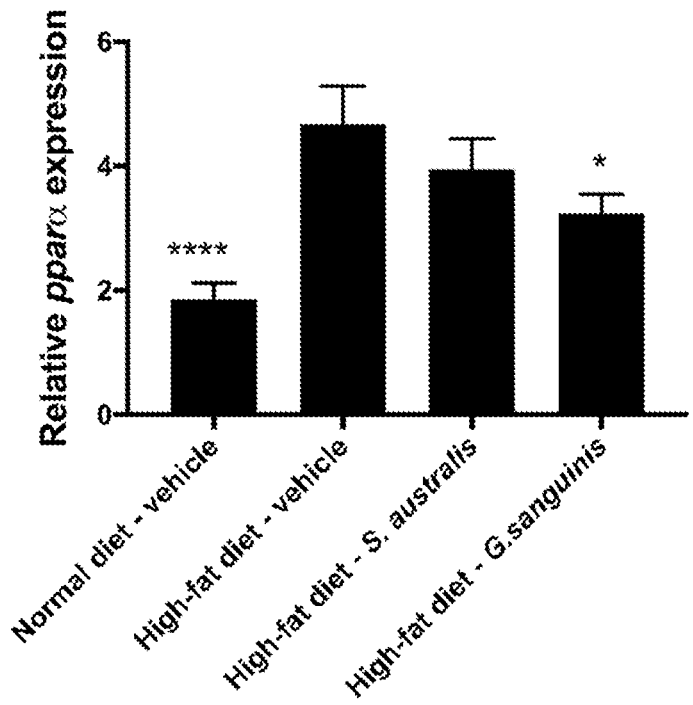
FIGS. 5A-5C show effects of treatment with *G. sanguinis* on expression of genes associated with lipid oxidation; peroxisome proliferator activated receptor alpha (ppara.
Figure 5B:
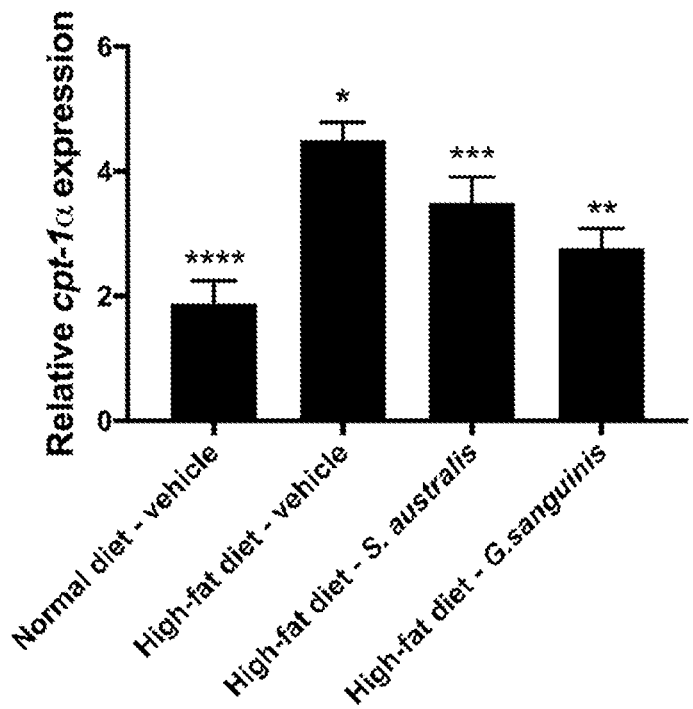
Figure 5C:
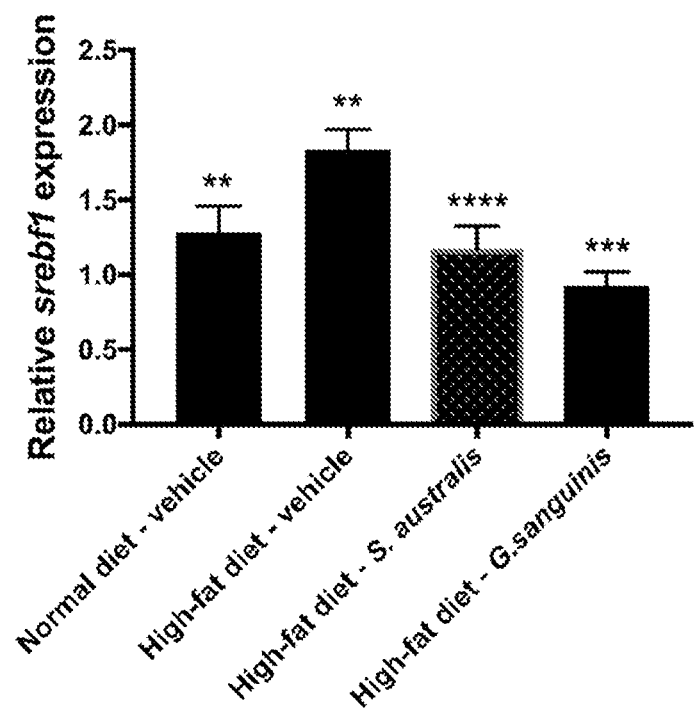

Samples obtained from the mice were also processed to analyze expression of genes that are associated with glucose and fat metabolism. Liver and brown adipose tissue was collected from the mice and snap frozen by immersion in liquid nitrogen then stored at $-80°$ C. Total RNA was prepared from the tissues, cDNA was prepared by reverse transcription, and real-time PCR was performed using forward and reverse primers specific for the genes ppara (peroxisome proliferator activated receptor alpha), cpt-1α (carnitine palmitoyltransferase 1A), and srebf1 (sterol regulatory element binding transcription factor 1), which are markers of lipid oxidation. Activation of these gene products is indicative of increased fat production. Results of this analysis are shown in FIG. 5A, FIG. 5B and FIG. 5C and demonstrate a decrease in the expression of all 3 genes in the livers of animals treated with G *sanguinis*.

Example 4

Treatment of Type 2 Diabetes with a Composition Comprising *G. sanguinis*

A clinical trial to study the effects of a live biotherapeutic product which contains *G. sanguinis* is carried out to studied the effects of this composition for treating type 2 diabetes. The study includes measurements of the *G. sanguinis* bacteria in fecal matter, glucose tolerance and insulin sensitivity before and after treatment.

The study is a randomized, placebo-controlled, double-blinded trial. Twenty-four adults diagnosed with Type 2 diabetes are randomly assigned to a test group (n=12) and a control group (n=12). Each subject in the test group is orally administered a capsule containing equal amounts of *G. sanguinis* ($\sim 10^8$-$10^{12}$ CFU) while the subjects in the control group receive a placebo capsule. Each subject in the test group is orally administered a capsule containing. Each subject is the test group is orally administered a placebo tablet. Capsules are administered to each subject q.d. in the morning for a period of 4 weeks. The subjects are instructed to abstain from fermented dairy products during the weeks of treatment. Strenuous physical exercise is avoided for 48 hours before the oral glucose tolerance test (OGTT). Oral anti-diabetics and statins are withheld for 1 week and all other medications for 24 hours.

Stool samples are collected within 24 hours prior to the first administration of a capsule and on the last day of administration. Samples are kept at $5°$ C. for no longer than 24 hours, and are stored at $-80°$ C. until analyzed in a laboratory. Total bacterial DNA and genomic DNA is extracted from the fecal samples.

To determine the levels of *G. sanguinis* in the stool samples, gene sequences specific for *G. sanguinis* are PCR-amplified, confirmed by DNA sequencing, then analyzed by real-time PCR to determine the level of *G. sanguinis* in the stool samples of each subject.

OGTTs are administered at the start and end of the study to determine effects of the treatment of glucose tolerance. Each subject is given an oral glucose tolerance test (OGTT) the day prior to the first oral administration of the capsule and on the last day of administration. Subjects drink 75 g glucose diluted in 500 ml water over 5 minutes. Plasma glucose is measured at baseline, and at 1 and 2 hours after the glucose administration.

The effects of treatment on insulin resistance is measured using the hyperinculinemic-euglycemic clamp technique. Generally, after an overnight fast, subjects report to the laboratory and an intravenous catheter for administration of insulin, glucose and electrolyes is place in an antecubital vein. A retrograde catheter is inserted into a dorsal vein in the contralateral hand.

The duration of the clamp is 180 minutes. Insulin (100 IU/ml) is infused continuously at a rate of 0.120 IU/min per $m^2$. Plasma glucose are measured at 5 minute intervals during hour 1 and at 10 minute intervals during the hours 2 and 3. Plasma glucose levels are targeted at $5.0\pm0.2$ mmol/l by adjusting the infusion rates of glucose (200 g/1) on a computer-controlled infusion pump. M, the whole-body metabolic rate of glucose, is calculated from the glucose infusion rate in the interval between 120 and 180 min according to the equations of DeFronzo et al. (1979, Am J Physiol 237:E214-E223). Isotonic saline with K is continuously infused to avoid hypokalemia. Blood for analysis of insulin is drawn every 30 minutes into EDTA-containing tubes and centrifuged instantly. Plasma is stored at $-80°$ C. until analysis.

Although the foregoing invention has been described in some detail by way of illustration and examples, which are for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention.

The invention claimed is:

1. A method for treating a metabolic disorder in a subject in need thereof, said method comprising:
    a) administering to the subject a composition comprising:
        i) an active ingredient consisting of a therapeutically effective amount of an isolated *Gemella sanguinis* (*G. sanguinis*) bacterial strain; and
        ii) a pharmaceutically acceptable carrier, wherein the only active ingredient is *G. sanguinis*.

2. The method of claim 1, wherein the *G. sanguinis* is viable.

3. The method of claim 1, wherein the metabolic disorder is selected from the group consisting of hyperglycemia, type 2 diabetes, and a combination thereof.

4. The method of claim 1, wherein the metabolic disorder is not type 1 diabetes.

5. The method of claim 1, wherein the subject has presented with a fasting blood glucose level of greater than about 125 mg/dL.

6. The method of claim 1, wherein the subject has presented with a 2-hour value for a 75 gram oral glucose tolerance test of greater than about 140 mg/dL.

7. The method of claim 1, wherein the therapeutically effective amount of *G. sanguinis* comprises about $1\times10^7$ to $1\times10^{12}$ colony forming units (CFU) of *G. sanguinis*.

8. The method of claim 1, wherein the method comprises administering the composition to the subject once, twice or three times per day over a time period of at least about 1-52 weeks.

9. The method of claim 1, wherein the method results in a reduction of the subject's fasting blood glucose level of at least about 5% of the fasting blood glucose level of the subject prior to the first administration of the composition.

10. The method of claim 9, wherein the reduction of the subject's fasting blood glucose level is measured at 1 month, 2 months, 3 months, 4 months, 5 months, 6 months, 7 months, 8 months, 9 months, 10 months, 11 months, or 12 months after the first administration of the composition.

11. The method of claim 1, wherein the *G. sanguinis* bacterial strain has a 16S rRNA sequence that is at least 97% identical to SEQ ID NO: 1.

12. The method of claim 1, wherein the *G. sanguinis* bacterial strain has a 16S rRNA sequence that is at least 98% identical to SEQ ID NO: 1.

13. The method of claim 1, wherein the *G. sanguinis* bacterial strain has a 16S rRNA sequence that is at least 99% identical to SEQ ID NO: 1.

14. A method for reducing glucose levels in the blood of a subject in need thereof, the method comprising: administering to the subject a composition comprising:

i) an active ingredient consisting of a therapeutically effective amount of an isolated *G. sanguinis* bacterial strain; and ii) a pharmaceutically acceptable carrier, wherein the only active ingredient is *G. sanguinis*.

15. The method of claim 14, wherein the blood of the subject has a glucose level greater than 125 mg/dL prior to administering the composition.

16. The method of claim 14, wherein the composition is formulated for oral ingestion.

17. The method of claim 14, wherein the composition is a food-based product.

18. The method of claim 14, wherein the composition is formulated as a tablet, capsule, a liquid, or a liquid suspension.

19. A method for treating a metabolic disorder in a subject in need thereof, said method comprising:

a) administering to the subject a composition comprising:

i) a therapeutically effective amount of an isolated *Gemella sanguinis* (*G. sanguinis*) bacterial strain; and ii) a pharmaceutically acceptable carrier, wherein the *G. sanguinis* bacterial strain has a 16S rRNA sequence that is 100% identical to SEQ ID NO: 1.

* * * * *

SEQUENCE LISTING

<160> NUMBER OF SEQ ID NOS: 1

<210> SEQ ID NO 1
<211> LENGTH: 1510
<212> TYPE: DNA
<213> ORGANISM: Gemella sanguinis

<400> SEQUENCE: 1

```
gacgaacgct ggcggcgtgc ctaatacatg caagtcgagc gaagttttc  tggtgcttgc      60 actagaaaaa cttagcggcg aacgggtgag taacacgtaa agaacctgcc tcatagacgg     120
ggacaactat tggaaacgat agctaatacc ggataacagc ataaatcgca tgatatatgt     180
ttaaaagttg gtttcggcta acactatgag atggctttgc ggtgcattag ctagttggtg     240
gggtaaaggc ctaccaaggc gacgatgcat agccgacctg agagggtgat cggccacact     300
gggactgaga cacggcccag actcctacgg gaggcagcag tagggaatct tccgcaatgg     360
gcgaaagcct gacggagcaa cgccgcgtga gtgaagaagg atttcggttc gtaaagctct     420
gttgttaggg aagaatgatt gtatagtaac tatatacagt agagacggta cctaaccaga     480
aagccacggc taactacgtg ccagcagccg cggtaatacg taggtggcaa gcgttgtccg     540
gaattattgg gcgtaaagcg cgcgcaggtg gtttaataag tctgatgtga aagcccacgg     600
ctcaaccgtg gagggtcatt ggaaactgtt aaacttgagt gcaggagaga aaagtggaat     660
tcctagtgta gcggtgaaat gcgtagagat taggaggaac accagtggcg aaggcggctt     720
tttggcctgt aactgacact gaggcgcgaa agcgtgggga gcaaacagga ttagataccc     780
tggtagtcca cgccgtaaac gatgagtgct aagtgttggt ctcataagag atcagtgctg     840
cagctaacgc attaagcact ccgcctgggg agtacgaccg caaggttgaa actcaaagga     900
attgacgggg acccgcacaa gcggtggagc atgtggttta attcgaagca acgcgaagaa     960
ccttaccaag tcttgacata ctgtgaggac acaagagatt gtgttgttct gacctttggt    1020
tagacacaga tacaggtggt gcatggttgt cgtcagctcg tgtcgtgaga tgttgggtta    1080
agtcccgcaa cgagcgcaac ccctatgtct agttgccagc agtaagatgg ggactctaga    1140
cagactgcca gtgataaact ggaggaaggc ggggatgacg tcaaatcatc atgcccctta    1200
tgacttgggc tacacacgtg ctacaatgga taggaacaaa gagaagcaaa ctcgcgagag    1260
caagcaaacc tcataaaact attctcagtt cggattgtag tctgcaactc gactacatga    1320
agctggaatc gctagtaatc gcgaatcaga atgtcgcggt gaatacgttc ccgggtcttg    1380
tacacaccgc ccgtcacacc acgagagttt gtaacacccg aagacggtgg cctaaccttt    1440
aaggagggag ccggtcacgg tgggacagat gattggggtg aagtcgtaac aaggtagccg    1500
tatcggaagg                                                         1510
```